US006103253A

United States Patent [19]

Hoffmann et al.

[11] Patent Number: 6,103,253

[45] Date of Patent: Aug. 15, 2000

[54] SPRAYABLE, FILM-FORMING ACTIVE SUBSTANCE RELEASE SYSTEMS FOR APPLICATION TO PLANTS

[75] Inventors: Hans-Rainer Hoffmann; Michael Roreger, both of Neuwied; Malgorzata Kloczko, Linz, all of Germany

[73] Assignee: LTS Lohmann Therapie-Systeme, GmbH, Neuwied, Germany

[21] Appl. No.: 08/809,311

[22] PCT Filed: Aug. 12, 1995

[86] PCT No.: PCT/EP95/03205

§ 371 Date: May 23, 1997

§ 102(e) Date: May 23, 1997

[87] PCT Pub. No.: WO96/06527

PCT Pub. Date: Mar. 7, 1996

[30] Foreign Application Priority Data

Aug. 27, 1994 [DE] Germany .............................. 44 30 449

[51] Int. Cl.[7] .................................................... A01N 25/24

[52] U.S. Cl. .......................... 424/407; 424/405; 424/409; 424/486; 523/122; 524/37; 524/599

[58] Field of Search ................................. 524/37–39, 46, 524/599; 523/122, 124, 128; 424/405, 407, 409, 7, 11, 719, 786, 788

[56] References Cited

U.S. PATENT DOCUMENTS

| | | | |
|---|---|---|---|
| 1,909,991 | 5/1933 | Weihe et al. | 524/39 |
| 3,090,694 | 5/1963 | Pereny et al. | 524/39 |
| 4,623,540 | 11/1986 | Costanza | 424/81 |
| 4,923,698 | 5/1990 | Rodero | 424/405 |
| 5,720,967 | 2/1998 | Hori-Hisbitts et al. | 424/405 |

FOREIGN PATENT DOCUMENTS

| | | |
|---|---|---|
| 31497/84 | 3/1984 | Australia . |
| 2804563 | 8/1979 | Germany . |
| 1364267 | 1/1988 | U.S.S.R. . |
| 8700399 | 1/1987 | WIPO . |

OTHER PUBLICATIONS

Ziv et al., *Plant Disease*, vol. 67, No. 2, Feb. 1983, pp. 212–214.

Kamp, *HortScience*, vol. 20(5) Oct., 1985 pp. 879–881.

*Primary Examiner*—Neil S. Levy
*Attorney, Agent, or Firm*—Wenderoth, Lind & Ponack, LLP

[57] ABSTRACT

A sprayable, film-forming active substance preparation for the application to plants is characterized by the fact that films which can be produced thereof are pressure-sensitive adhesive, water-insoluble, and at least partially biodegradable.

29 Claims, No Drawings

SPRAYABLE, FILM-FORMING ACTIVE SUBSTANCE RELEASE SYSTEMS FOR APPLICATION TO PLANTS

BACKGROUND OF THE INVENTION

The present invention relates to a sprayable, film-forming preparation, for the systemic administration of biologically active substances to plant organisms.

Active substance formulations normally used for plants are emulsion concentrates, suspension concentrates, or so-called wettable powders which are applied by means of different sprayers, spargers, or nebulizing devices (e.g. spray bottles). However, these conventional preparations entail the disadvantage that active substance losses occurring during their application contribute to the contamination of the environmental sections (air, earth, water). This problem is caused by the spray flowing or dripping down the plant surfaces, by rain water washing the spray off, and by the spray drift during application. Their insufficient retention (adherence) and the poor wettability of plant surfaces are further disadvantages of these active substance formulations. These deficiencies frequently interfere with achieving the desired effect.

In the past, many attempts were made to minimize these drawbacks in order to optimize the use of spray agents. According to the art, these attempts can be summarized as follows:

1. Application properties of sprays are improved by adding different substances, such as surface-active agents, substances to prevent drying up, re-humidifying agents, hygroscopic additives, foamers, and in particular adhesion promoters.
2. Selective positioning to plant surfaces is considerably facilitated by loading the spray electrostatically.
3. The retention and wetting properties can be improved by modifying the size of droplets, the spraying pressure, and the spraying distance.

However, none of these measures provide a satisfactory solution with respect to spray drift and environmental impact.

In order to overcome this disadvantage, improved active substance release systems were developed which represent an alternative to conventional sprays. These are depot formulations in the form of flat-shaped, patch-like, adherent or pressure-sensitive adhesive systems which are applied to the plant's shoot axis. These administration forms for active substances effectively overcome the problem of active substance losses and the resulting environmental pollution; however, their use involves a lot of other problems mainly caused by their application. With this kind of device it is extremely important to dimension the size of the contact surface to the plant such that the device does not project past any part of the plant. In case of plants, the growth of which limits the choices of application site, e.g. those completely covering the soil, the application of a device is very difficult. Also, the application of these systems to plants whose surfaces have spines or thorns must be regarded as critical.

In addition, there are problems with respect to using these systems in plants excessively growing in thickness; if the carrier foil is insufficiently stretchable, the application around the stems involves the risk that the plant becomes strangled or that the system grows into the shoot axis, this may damage the underlying tissue layers.

Finally, the use of such systems takes a relatively great deal of time and work not only with respect to the application, but also afterwards since they must be removed when the treatment is completed. Moreover, there is the cost-increasing problem of waste disposal.

According to the state of the art one can say in general terms that there has been considerable progress with respect to the reduction of the required active substance expenditure, the frequency of application, and the undesired effects on other organisms, but that this is accomplished at the expense of other properties.

Film-forming formulations represent another kind of active substance release systems. These are known in the art from the following patents SU 1364267, DE 2804563, and U.S. Pat. No. 4,923,698.

The publication SU 1364267 relates to a film-forming formulation based on carboxymethylcellulose and is used in the storage of agricultural products, in particular in the preservation of fruits and vegetables. To this end, the crop product to be stored is treated by spraying or dipping to form a thin film on the surface of the plant organs; owing to its physical properties, this film protects the plants from unnecessary losses of water and therefore improves their storage life. However, there is no indication in this publication that this preparation contains active substances.

German patent DE 2804563 discloses an active substance-containing, film-forming preparation. It describes a formulation that comprises bird repellents and is used as an agent against bud feeding in useful and flowering shrubs. This is an aqueous polymer dispersion that is stirred into water together with the active substance during the preparation of the plant spray; but it can also be formulated as an active substance-containing wettable powder.

In both, cases the incorporated base polymers, such as homopolymers and copolymers of vinyl acetate or acrylic ester, serve as adhesives.

It is also known in the art to prepare an substance-containing, film-forming formulation, which is a preparation of rodent repellents based on an inorganic active substance absorber (e.g., kaolin, talc). The addition of polymeric adhesion promoters such as methyl or carboxymethylcellulose, polyvinyl alcohol, or urea, results in the formation of a water-insoluble film layer adhering to the plants' surfaces and provides protection against rodents owing to its content of repellents.

U.S. Pat. No. 4,923,698 relates to film-forming, nonpolymeric preparations of insecticides or insect repellents. In this case, a formulation based on a water-in-oil emulsion is proposed which comprises lubricants in addition to the bioactive substances. The lubricants ensure that the film formed by evaporation of a predominant portion of the oil and water phase has a property of rendering the movement of running insects on its surface impossible. In addition, the active substances contained in the film can considerably increase the outcome of pest control because of its direct influence on pests.

In connection with film-forming, sprayable active substance preparations it is finally referred to the articles in the technical journals Hort science (20,50:879–881) and Plant Disease (67:212–214), which describe the experimental use of such developments in plants to control leaf diseases.

These known active substance-containing sprayable formulations, which are capable of forming films, have the severe disadvantage that the films resulting after their application cover the plant surface only for a relatively short time; this is to be ascribed to their hydrophilic character. These formulations are not suitable for the systemic release of active substances to the plant organism because they lack the capability of adhering permanently. The active substances must be present on the plant surface for a sufficiently long time in order to supply the plant organism with the active substance in a concentration sufficient to develop persistent systemic action.

Moreover, it is not the main function of these formulations to administer active substances to the plant, but to provide an external protection of the plant against pests. For this reason, the known application systems do not offer a satisfactory solution of the above-mentioned problem with respect to the administration of biologically active substances to plant organisms.

Thus, the horticultural community wish for ecologically beneficial active substance depot preparations for plants, which are easy to handle, is still left open by the art.

BRIEF DESCRIPTION OF THE INVENTION

It is the object of the present invention to propose a sprayable, active substance-containing, film-forming, pressure-sensitive adhesive, water-insoluble, and at least partially biodegradable preparation that preferably does not pollute the environment and which provides active substance release systems combining the advantages of conventional spraying systems and those of the so-called controlled-release-formulations without having to accept their drawbacks.

Most surprisingly, this object is achieved with an active substance formulation, which is incorporated into a film forming polymer which is a pressure sensitive adhesive, insoluble in water and at least partially biodegradable.

DETAILED DESCRIPTION OF THE INVENTION

The term "sprayable, film-forming preparation/formulation" is used to mean preparations which form a film on the surface of a substrate after application on said substrate by means of spraying. The film's state of distribution may differ; it may be a continuous film, or a discrete film distributed in lumps, and also intermediary transient stages.

Films made of the active substance formulations according to the present invention advantageously are pressure-sensitive adhesive, insoluble in water, and at least partially biodegradable.

Polymers performing both the function of film formers and that of active substance carriers are essential components of formulations cry according to the present invention. Such film-forming, sprayable polymer solutions are known from human medicine. They are used as wound dressings instead of textile dressing materials and adhesive dressings and are called "spray plaster" in colloquial language.

Homopolymers or copolymers of esters of acrylic acid and/or methacrylic acid, e.g., methyl acrylate, ethyl acrylate, acrylic acid-n-butyl-ester, and methacrylic methyl ester, are used as film-forming substances for the production of formulations according to the present invention. Moreover, other suitable polymers are cellulose derivatives with a degree of substituion of $\leqq 2$ such as ethylcellulose, cellulose butyrate or cellulose acetate, as well as polyhydroxy butyrate and polyhydroxy valerate.

The preparations according to the present invention are physical active substance/polymer-combinations which are present as a solution or emulsion. They are sprayed on a plant surface as aerosols and form thin, coherent, active substance-containing, and waterinsoluble films after evaporation of the solvents or emulsifiers.

The nontoxic organic solvents contained in these preparations are highly volatile. In general, they have a boiling range of +50° C. to 180° C. If possible, their boiling point should not exceed 150° C. to prevent unnecessarily long drying periods of the formed film. Suitable solvents include ethyl acetate, chloroform, acetone, ethanol, or their mixtures. The amount of the solvent or solvent mixture must be chosen such that the total preparation has a relatively low viscosity ensuring perfect spraying without formation of ropes.

In addition, the preparations according to the present invention must be perfectly aerosolizable and stable during storage in aerosol containers. Suitable propellants include light hydrocarbons, such as propane, butane, isobutane, and their mixtures in the form of a liquefiable gas. The halogenated hydrocarbons frequently used as propellant in the past shall not be used any longer because of their high ozone-destructive potential. Nitrogen, carbon dioxide, or dinitrogen monoxide may be used as blowing gases instead of light hydrocarbons.

The total amount of the solids mixture used as film former and active substance carrier system shall amount to 0.5 to 10%-wt., preferably 4 to 6%-wt., relative to the total preparation including propellant.

An important advantage of the active substance formulation according to the present invention is the fact that the formed films are pressure-sensitive adhesive. This efficiently counteracts the serious disadvantage of conventional techniques, i.e., the insufficient retention. The active substance-containing films resulting from these formulations preferably exhibit permanent adhesiveness. They immediately and permanently adhere to plant surfaces and thus ensure intimate contact to the terminal tissue of the plant; this contact is absolutely necessary for an optimum active substance release. In particular, if a long-term, sustained active substance supply is required, this property gains special importance. The high adhesive capacity is relatively temperature-independent in the application area. The stability of the films is also ensured in this area. For this reason, they are suitable both for the application to plants in the interior and for outdoor uses.

The pressure-sensitive adhesive properties of the film bring about additional advantages with respect to application, in particular in plant protection. Owing to the immediate adhesive power these films may serve as mechanical barrier or trap for numerous destructive insects which adhere to the film surface at the slightest touch. Since the films comprise active substances, pests (e.g., fungus spores or insects) will immediately come into contact with the active substance so that a harmful action is prevented.

Pressure-sensitive adhesive properties may be achieved by using suitable polymers as active substance carrier. These mainly include mixed copolymers of acrylic acid and acrylic esters, in particular alkyl acrylate having 4 to 12 carbon atoms in the alkyl group, for example, 2-ethylhexyl acrylate, n-butyl acrylate, and isooctyl acrylate.

If polymers are used which are not pressure-sensitive adhesive, suitable auxiliaries must be added to obtain the desired properties. Resin-like substances, such as modified natural resins, such as colophony and its derivatives, polyterpene resins, hydrocarbon resins, and coumarone-indene resins will serve this purpose. Particularly suitable are colophony esters (such as Foral® 85 and Staybelite®Ester 10) since it has an excellent compatibility with polyacrylates. The amount of resin added depends on the desired adhesive properties. There is an upper limit because the cohesion of the formed films is too low where the resin proportion is excessively high. The amount may vary from 1.0 to 20%-wt., preferably 5 to 10%-wt., relative to the solids content of the preparation.

Another advantage of the preparations according to the present invention lies in the fact that the formed films are insoluble in water. This is of particular importance because the films adhere to the plant surfaces even during high-rainfall periods. For this reason the adhesive strength of the films does not change over a desired treatment period.

The water resistance results from hydrophobic properties of the film-forming substance. In addition to polyacrylates, polyhydroxy butyrate and hydroxy butyrate-hydroxyvalerate-copolymers, as well as ethylcellulose and cellulose butyrate and cellulose acetate may be used as suitable film-forming components of the preparations according to the present invention. Moreover, they stand out for biodegradability, rendering them particularly suitable for use in the production of the preparations according to the present invention.

Films formed on plant surfaces from preparations according to the present invention must preferably be biodegradable. This means that they are partially or completely decomposed by the action of a biologically active environment (microorganisms). This property is particularly advantageous since the films, owing to their good pressure-sensitive adhesiveness, may remain on the plants as active substance depots for longer periods of time (e.g., one vegetation period) without having to be removed later. The degree of biodegradability can be controlled by the choice of polymer. The user of these formulations can therefore save a great deal of time and work and simultaneously has the advantage of a persistent active substance supply. This combination of the above-mentioned properties renders the preparations according to the present invention, clearly superior to active substance release systems described in the art.

The active substances contained in the films according to the present invention are released in a controlled manner, the release taking place by diffusion.

Active substances which can be released to plants by means of the preparations according to the present invention are those influencing processes in the animal or plant organism. Insecticides, fungicides, acaricides, bactericides, and growth regulators are to be mentioned as systemically active plant protection agents in the first place.

Systemic insecticides include, for example, butocaroxim, dimethoate, fenoxycarb, methamyl, oxamyl, oxydemeton-methyl, pirimicarb, or propoxur.

Systemic fungicides include, for example, benomyl, bromuconazole, bitertanole, etaconazole, flusilazol, furalaxyl, fosetyl-A1, imazalil, metalaxyl, penconazole, propiconazole, thiabendazol, triadimefon, triadimenol, or triforine.

1Systemic acaricides include, for example, clofentizine, fenbutatin oxide, and hexythiazox.

Systemic growth regulators include, for example, ethephon and β-indolylacetic acid (IAA).

Flumequine, for example, is to be mentioned among the systemic bactericides.

Moreover, the preparations according to the present invention may comprise active substances which do not act systemically in the plant, but remain on the plant surface and therefore have a contact action on pests. It is possible, for example, to incorporate contact fungicides belonging to the family of dithiocarbamates, such as maneb, zineb, or mancozeb, into the preparations according to the present invention in order to protect plant surfaces from local fungus infections (fungi causing false mildew, organisms causing spotting on leaves, various rust diseases).

Bird and insect repellents represent another application example of bioactive substances which do not develop their action via the plant. These may also be applied on plant surfaces by means of the preparations according to the present invention and can thus develop their action on the respective pest.

Active substances may be present in preparations according to the invention either individually or in a mixture. They may be dissolved or dispersed in the polymer matrix. A preferred embodiment of formulations according to the present invention has the following ingredients:

a) 1.0 to 10.0%-wt. of solids, the solids comprising:
   0.5 to 8.0%-wt. of at least one polymer
   0.5 to 5.0 of at least one active substance
   0.0 to 2.0%-wt. of formulation auxiliaries, relative to the total weight of the preparation, b) 0.5 to 80%-wt. of at least one volatile organic solvent c) 0.5 to 80%-wt. of at least one liquefied gas propellant.

Preparations according to the present invention may comprise as auxiliary agents penetration enhancers, tackifiers, emulsifiers, and plasticizers. The function of these auxiliary agents is, on the one hand, to offer the active substance to the plant in a suitable physical-chemical form and, on the other hand, to produce the optimum effect of the potency inherent in an active substance.

Penetration enhancers intensify the diffusion of a bioactive substance into the conducting system of the plant. For this purpose, the following substances may be added: alkylsulfates, alkyl sulfonates, fatty acids, fatty acid salts of multivalent metals, fatty acid esters, amine oxides, mono-, di- or triglycerides, long-chain alcohols, salicylic acid, 2-pyrrolidone derivatives, or urea.

Adhesive resins are suitable tackifiers. Colophony esters (Staybelite® Ester 10) and synthetic hydrocarbons (such as Escorez® 1102 F) are particularly suitable.

Suitable emulsifiers include, for example, higher fatty alcohols, partial fatty acid esters, polyvalent alcohols, partial fatty acid esters of sugars, polyethyleneglycol fatty acid esters, polyethyleneglycol sorbitan-fatty acid esters, as well as phospholipides, quaternary ammonium compounds, and pyridinium compounds.

Suitable plasticizers include low-molecular polyethylene alcohols, glycerol esters, mono- and polyvalent alcohols, fats, or waxes.

The formulations according to the present invention may serve to administer bioactive substances to plants, which have both a systemic and a local action. Plant protection is a preferred field of application of the preparations according to the present invention. The following examples are given to illustrate the present invention. Any indications as to quantities, proportions, and percentages relate to the total weight of the preparation (including propellant), unless otherwise stated.

EXAMPLE 1

4.5 parts by weight of a 2-ethylhexyl acrylatelacrylic acid-copolymer having a molar mass of 750,000 dalton is dissolved in a pressure vessel under heating and stirring in 44 parts by weight of ethyl acetate. After addition of 0.9 parts by weight of colophony resin (Foral®(85), used as tackifier, 0.6 parts by weight of the active substance triticonazole are dispersed in the mass thus obtained. This active substance-containing polymer solution, whose relative viscosity at 25° C. amounts to 0.58 Pa.s (according to Brookfield LVF/measuring body), can be filled into an aerosol container under addition of 50 parts by weight of same portions of butane, propane, and isobutane.

Example 2

5 parts by weight of the active substance fenarimole together with 0.5 parts by weight of N-methyl-2-pyrrolidone are added to 29.5 parts by weight of a conventionally obtained mixed polymer consisting of 75%-wt. of poly-2-ethylhexyl acrylate, 15%-wt. of polyacrylic acid, and 10%-wt. of polymethyl methacrylate, and which is present as a 48%-wt.-polymer solution in a solvent mixture consisting of equal parts by weight of ethyl acetate and ethanol. The added active substance is homogeneously distributed in the mass under constant stirring. After addition of 65 weight percentage of liquefied butane, the active substance-containing polymer solution is filled into an aerosol container.

What is claimed is:

1. A sprayable composition to be applied to plants comprising an effective amount of a plant protective active substance and a polymer within an organic solvent which is volatile and non-toxic in the surrounding atmosphere, wherein the composition forms an active substance containing adhesive film when applied to a plant, said polymer is film-forming, a contact adhesive, water-insoluble, at least partially biodegradable under atmospheric conditions and is selected from a cellulose derivative with a degree of substitution of ≦2 comprising a cellulose ether, a cellulose ester or a cellulose-acetate-butyrate mixed ester, or a homopolymer or a copolymer of hydroxybutanoic acid or hydroxyvaleric acid.

2. A sprayable composition to be applied to plants which forms an active substance containing adhesive film when applied to a plant comprising (a) 1.0 to 10.0% wt. of solids comprising, based on the total weight of the composition:

(i) 0.5 to 8.0% of at least one polymer which is film-forming, a contact adhesive water insoluble, at least partially biodegradable under atmospheric conditions and is selected from a cellulose derivative with a degree of substitution of ≦2 comprising a cellulose ether, a cellulose ester or a cellulose-acetate-butyrate mixed ester, or a homopolymer or a copolymer of a hydroxybutanoic acid or hydroxy valeric acid;

(ii) 0.5 to 5.0% wt. of a plant protective active substance; and (iii) 0.0 to 2.0% wt. of an auxiliary agent; and (b) 0.5 to 80% wt. of at least one organic solvent which is volatile and nontoxic organic in the surrounding atmosphere combined with 0.5 to 80% wt. of at least one liquified gas propellant;

wherein said plant protective agent and polymer are within the organic solvent.

3. The sprayable composition according to claim 2, wherein the auxiliary agent is a penetration enhancer, a tackifier, an emulsifier and/or a plasticizer.

4. The sprayable composition according to claim 2 wherein the active substance is selected from the group consisting of an insecticide, a fungicide, a bactericide, an acaricide and a plant growth regulator; wherein said insecticide is selected from the group consisting of butocaroxim, dimethoate, fenoxycarb, methamyl, oxamyl, oxydemeton-methyl, pirimicarb and propoxur;

said fungicide is selected from the group consisting of benomyl, bromuconazole, bitertanole, etaconazole, flusilazol, furalaxyl, fosetyl-A1, imazalil, metalaxyl, penconazole, propiconazole, thiabendazol, triadimefon, triadimenol and triforine;

said bactericide is flumequine;

said acaricide is selected from the group consisting of clofentizine, fenbutatin oxide and hexythiazox; and said plant growth regulator is selected from the group consisting of ethephon and β-indolylacetic acid (IAA).

5. The sprayable composition according to claim 2, additionally comprising an active substance having contact action selected from the group consisting of a fungicide and an insect repellent; wherein said fungicide having contact action is selected from the group consisting of dithiocarbamates, ziram, zineb, nabam, marcozeb and thiram; and said insect repellent having contact action is selected from the group consisting of dimethylphthalate, indalone or N,N-diethyl-meta-toluamide.

6. A method of achieving protection of plants comprising applying the sprayable composition of claim 2 onto a plant.

7. The composition of claim 1, wherein the active substance is released from the composition in a controlled manner by diffusion.

8. The sprayable composition according to claim 1 comprising a penetration enhancer, a tackifier, an emulsifier and/or a plasticizer as an auxiliary agent.

9. The sprayable composition according to claim 1, wherein the active substance is selected from the group consisting of an insecticide, a fungicide, a bactericide, an acaricide and a plant growth regulator.

10. The sprayable composition according to claim 9, wherein the insecticide is selected from the group consisting of butocaroxim, dimethoate, fenoxycarb, methamyl, oxamyl, oxydemeton-methyl, pirimicarb and propoxur.

11. The sprayable composition according to claim 9, wherein the fungicide is selected from the group consisting of benomyl, bromuconazole, bitertanole, etaconazole, flusilazol, furalaxyl, fosetyl-A1, imazalil, metalaxyl, penconazole, propiconazole, thiabendazol, triadimefon, triadimenol and triforine.

12. The sprayable composition according to claim 9, wherein the bactericide is flumequine.

13. The sprayable composition according to claim 9, wherein the acaricide is selected from the group consisting of clofentizine, fenbutatin oxide and hexythiazox.

14. The sprayable composition according to claim 9, wherein the plant growth regulator is selected from the group consisting of ethephon and β-indolylacetic acid (IAA).

15. The sprayable composition according to claim 1, additionally comprising an active substance having contact action selected from the group consisting of a fungicide and an insect repellent.

16. The sprayable composition according to claim 15, wherein the fungicide is selected from the group consisting of dithiocarbamates, ziram, zineb, nabam, marcozeb and thiram.

17. The sprayable composition according to claim 15, wherein the insect repellent is selected from the group consisting of dimethylphthalate, indalone or N,N-diethyl-meta-toluamide.

18. The sprayable composition according to claim 1, wherein the active substance is in a controlled release form.

19. The sprayable composition according to claim 9, wherein the active substance is in a controlled release form.

20. The sprayable composition according to claim 8, wherein the active substance is selected from the group consisting of a insecticide, a fungicide, a bactericide, an acaricide and a growth regulator.

21. The sprayable composition according to claim 20, wherein the active substance is in a controlled release form.

22. The sprayable composition according to claim 9, additionally comprising an active substance having contact action selected from the group consisting of a fungicide and insect repellents.

23. A method of achieving protection of plants comprising applying the sprayable composition of claim 1 onto a plant.

24. The method of claim 23, wherein the sprayable composition is applied to the plant surface as a thin layer.

25. A method of achieving protection of plants comprising applying the sprayable composition of claim 9 onto a plant.

26. A method of achieving protection of plant, comprising applying the sprayable composition of claim 18 onto a plant.

27. A method of achieving protection of plants comprising applying the sprayable composition of claim 19 onto a plant.

28. A method of achieving protection of plants comprising applying the sprayable composition of claim 20 onto a plant.

29. A method of achieving protection of plants comprising applying the sprayable composition of claim 22 onto a plant.

* * * * *